United States Patent [19]

Roelandt et al.

[11] Patent Number: 5,207,228
[45] Date of Patent: May 4, 1993

[54] DUAL PORT THERMODILUTION CATHETER

[75] Inventors: Robert Roelandt, Affligem, Belgium; Miriam Taimisto, Sierra Madre; Clement E. Lieber, Yorba Linda, both of Calif.

[73] Assignee: Baxter International Inc., Deerfield, Ill.

[21] Appl. No.: 823,092

[22] Filed: Jan. 21, 1992

[51] Int. Cl.$^5$ .................................................. A61B 5/02
[52] U.S. Cl. ....................................... 128/713; 128/736
[58] Field of Search ........................... 128/668, 713, 736

[56] References Cited

U.S. PATENT DOCUMENTS

| | | | |
|---|---|---|---|
| 3,726,269 | 4/1973 | Webster, Jr. | 128/713 |
| 4,563,181 | 1/1986 | Wijayarathna et al. | 604/280 |
| 4,573,476 | 3/1986 | Ruiz | 128/658 |
| 4,632,125 | 12/1986 | Webler et al. | 128/692 |
| 4,696,304 | 9/1987 | Chin | 128/673 |
| 4,718,423 | 1/1988 | Willis et al. | 128/634 |
| 4,721,115 | 1/1988 | Owens | 128/713 |
| 4,869,263 | 9/1989 | Segal et al. | 128/713 X |
| 4,941,475 | 7/1990 | Williams et al. | 128/713 X |
| 5,009,234 | 4/1991 | Alf | 128/736 X |

Primary Examiner—Randall L. Green
Assistant Examiner—Mary Beth O. Jones
Attorney, Agent, or Firm—William Nieman; Bruce M. Canter

[57] ABSTRACT

A catheter for monitoring heart function comprises a catheter tube having a plurality of lumens. The catheter includes an inflatable balloon at a distal tip of the catheter tube for positioning the catheter in a wedged position within a pulmonary artery within the heart of a patient. Dual injectate ports are formed in a side wall of the catheter tube. Each port communicates with a respective injectate lumen carried in the catheter tube. When inserted into the heart of a patient, either the first or second injectate port is positioned within the desired distance from the tricuspid valve for thermodilution depending upon the size of the heart. Thermodilution to obtain cardiac output and/or right heart ejection fraction is implemented by injecting injectate through the lumen associated with the port properly positioned relative the tricuspid valve and discharged through the corresponding port.

4 Claims, 5 Drawing Sheets

DUAL PORT THERMODILUTION CATHETER

FIELD OF THE INVENTION

The present invention relates to catheters, and, in particular, to catheters which utilize thermodilution techniques to measure cardiac output.

BACKGROUND OF THE INVENTION

Multiple lumen catheters are commonly used to measure and monitor cardiac output. In operation, the catheter is typically introduced into a central vein of a patient and advanced toward the right atrium through the superior or inferior vena cava. Once the distal tip of the catheter is positioned within the vena cava, a small balloon positioned over the distal tip is inflated through an inflation lumen provided in the catheter. The balloon carries the catheter along the flow of blood through the right atrium and right ventricle into the main pulmonary artery. The catheter continues to advance until a wedge position is reached within an individual pulmonary artery wherein the balloon seals off the inflow of blood through the artery. In this position, pulmonary artery wedge pressure measurements are commonly taken and the balloon then deflated.

Subsequent to balloon deflation, thermodilution techniques are frequently utilized to measure cardiac output. Using thermodilution, a bolus of cold saline injectate is injected through a port in communication with one lumen of the catheter into the blood stream, and the resulting temperature change is measured with a thermistor located at a distal end of the catheter. Right heart ejection fraction can also be measured with thermodilution techniques in a known manner by further monitoring the occurrence of contractions using electrodes which are positioned at the distal end of the catheter within the right ventricle.

To achieve optimum accuracy using thermodilution techniques, the injectate is injected into the right atrium in an abrupt manner so as to be evenly distributed and well mixed in the right ventricle prior to ejection through the pulmonary artery. Commonly, the injectate is injected through a port located approximately 5 cm proximal of the tricuspid valve, adjacent the right atrium. When injected in this manner, the injectate flows countercurrent to the blood flow from the inferior vena cava, and thorough mixing with the incoming blood is achieved. Often, the injectate port comprises plural openings to further assist in injectate mixing and distribution within the blood stream.

Because heart size varies from patient to patient, the location of the injectate port once the distal tip of the catheter is positioned within the individual pulmonary artery also varies. Often, the catheter must be manually repositioned prior to thermodilution in order to locate the injectate port at the desired distance from the tricuspid valve. Then, once the thermodilution process has been completed, the catheter must be repositioned at the desired location within the pulmonary artery. This repositioning increases the risk of infection, the risk of damage to the heart and pulmonary artery caused by wall perforation, and further increases the amount of time that must be spent by the attending physician to perform the desired procedures.

SUMMARY OF THE INVENTION

The present invention provides a cardiac output catheter having dual injectate ports. The catheter comprises a flexible catheter tube having a proximal and a distal end. The catheter tube includes a plurality of lumens including two injectate lumens which are in communication with the two injectate ports. An inflatable balloon located at the distal end of the catheter carries the catheter to a wedged position within a pulmonary artery when the catheter is inserted into the heart of a patient. Depending upon the size of the heart, either the first or second injectate port is positioned within the desired distance proximal the tricuspid valve for thermodilution, preferably within 2-5 cm of the valve. Thermodilution techniques to obtain cardiac output and/or right heart ejection fraction data are implemented by injecting a bolus of cold saline injectate through the lumen in communication with the injectate port properly positioned relative the tricuspid valve. The injectate is mixed with the blood flow in the right atrium and flows through the pulmonary artery past a thermistor at the distal end of the catheter which transmits data to appropriate electronic devices for measuring cardiac output and/or right heart ejection fraction.

In accordance with the present invention, a catheter for use in monitoring heart function is disclosed wherein the catheter comprises an inflatable balloon for positioning a distal end of the catheter in a pulmonary artery. The catheter additionally comprises plural lumens and corresponding plural injectate ports for injecting fluid proximal to the tricuspid valve of the heart, a first of said injectate ports being located closer to said balloon than a second of said injectate ports. The plural injectate ports are spaced to accommodate hearts of different sizes, whereby one of the injectate ports is positioned proximal to the tricuspid valve when said balloon is in said pulmonary artery. Each of the injectate ports may comprise an array of closely spaced openings.

The present invention further provides a method of using a thermodilution catheter comprising inserting the thermodilution catheter into the heart of a patient, positioning one of plural injectate ports in the catheter proximal to the tricuspid valve of the heart, positioning another of the plural injectate ports further away from the tricuspid valve than the one injectate port, and injecting fluid through the one of the plural injectate ports. The method may additionally comprise the subsequent steps of detecting an unintended change in position of the one injectate port relative to the tricuspid valve, and utilizing another of said injectate ports to inject the fluid.

In a further aspect of the invention, a method of manufacturing a thermodilution catheter having plural lumens and an inflatable balloon for positioning a distal end of the catheter in a pulmonary artery is disclosed comprising forming openings in a wall of said catheter to provide plural injectate ports for receiving fluid from plural lumens, respectively, and locating the injectate ports to accommodate hearts of different sizes such that one of the injectate ports is proximal to the tricuspid valve for a relatively large heart and another of the injectate ports is proximal to the tricuspid valve for a relatively small heart. In large hearts, the injectate port located in the right ventricle can be used for right ventricle (RV) pressure recording simultaneously to right ventricle ejection fraction (RVEF) measurement allowing definition of pressure volume points defining systolic and diastolic RV function. The dual port design augments visibility of catheter migration, and thus increases safety, by dual port pressure monitoring.

DETAILED DESCRIPTION OF THE INVENTION

Figure 1:
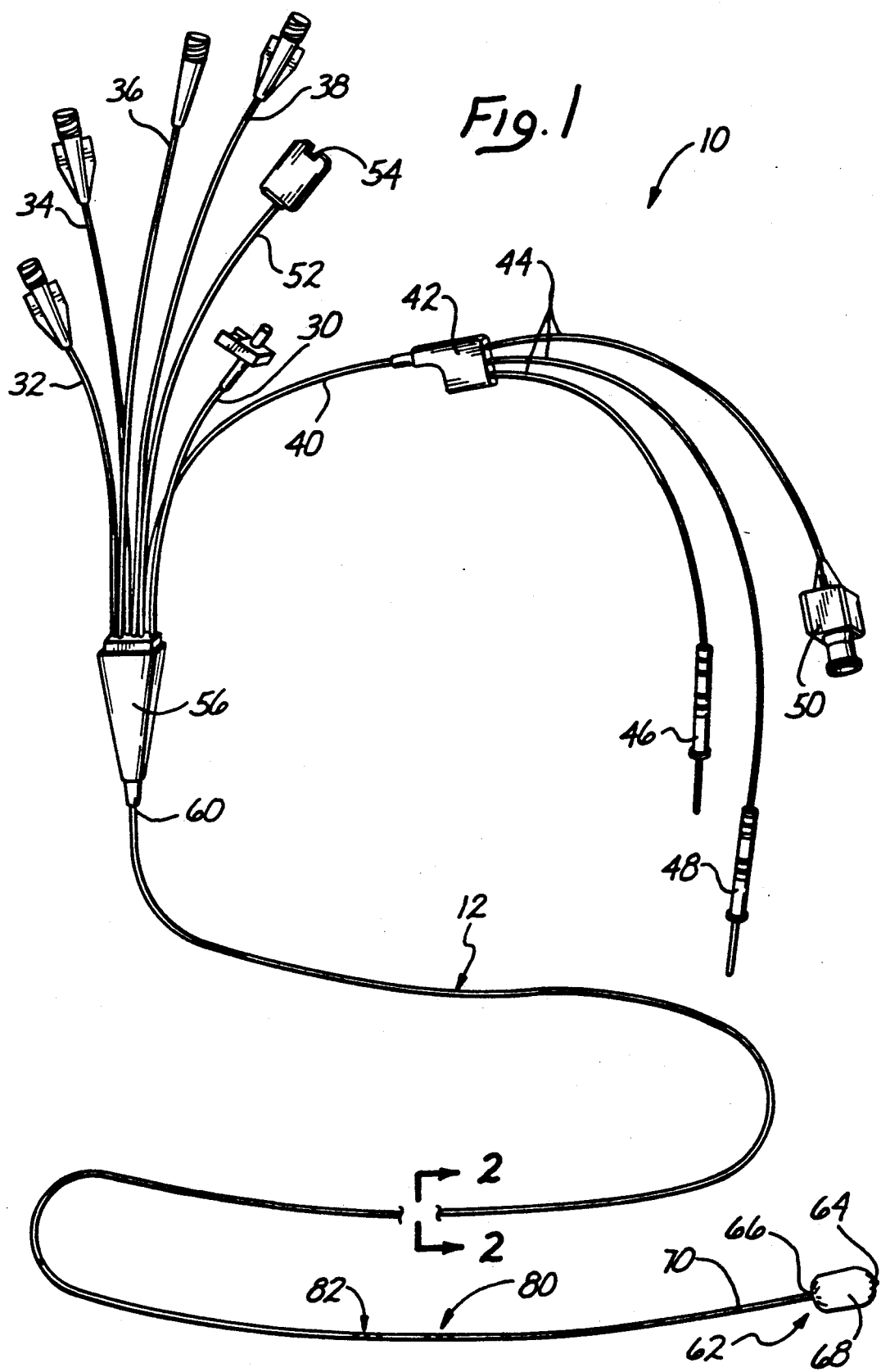
FIG. 1 is a perspective view of a cardiac output catheter in accordance with the present invention.
Figure 2:
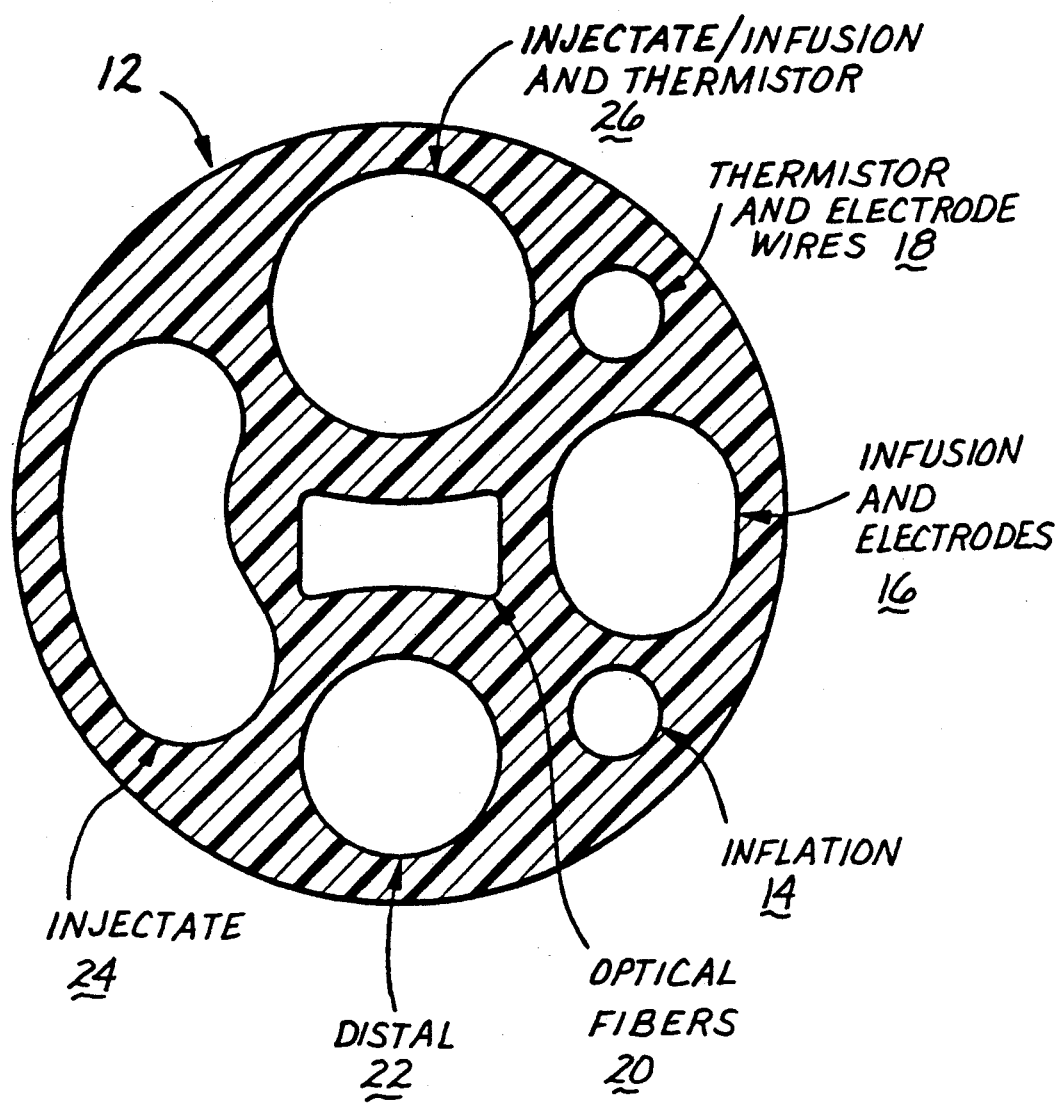
FIG. 2 is a cross-sectional view of the catheter taken along lines 2—2 of FIG. 1.

FIG. 1 illustrates a cardiac output catheter 10 for monitoring heart function in accordance with the present invention. The catheter comprises a flexible catheter tube 12 extruded from a biocompatible plastic material such as radiopaque polyvinylchloride. As shown in FIG. 2, the catheter tube 12 comprises a plurality of lumens, including a first smaller, circular lumen 14 for balloon inflation; a second smaller circular lumen 18 which carries thermistor and electrode wires; a substantially rectangular fiber optic lumen 20; a first larger, generally circular lumen 16 for infusion and for carrying electrode wires; a second larger, generally circular distal through lumen 22; a third larger, generally circular lumen 26 for infusion and injectate; and a generally kidney-shaped injectate lumen 28.

Referring to FIG. 1, a balloon inflation tube 30, an infusion tube 32, and a distal lumen tube 34 are fused to the catheter tubing 12 within the balloon inflation lumen 14, infusion lumen 16, and distal through lumen 22, respectively. Further, first and second injectate tubes 36, 38 are fused to the catheter tube 12 within the first and second injectate lumens 24, 26. A first insulating tube 40 is fused to the catheter tube 12 within the lumen 18 which carries the thermistor and electrode wires. The wires are separated in a connector 42 which couples the wires to individual conduits 44 having couplers 46, 48, 50 which can be attached to conventional electronic monitoring devices. A second insulating tube 52 is fused to the fiber optic lumen 20 and includes a connecter 54 for coupling the tube 52 and optical fiber carried therein to suitable monitoring equipment. A sleeve 56 covers the tubes 30, 32, 34, 36, 38, 40, 52 at their attachment to the catheter tube 12.

The catheter tube 12 comprises a proximal end 60, a portion of which is enclosed within the sleeve 56, and a distal end 62 opposite the proximal end 60. A port 64 at the distal tip communicates with the distal through lumen 22 and provides a means by which pressures within the body may be monitored. The distal end 62 of the catheter tube 12 further includes a balloon inflation port 66 which communicates with the balloon inflation lumen 14. An inflatable balloon 68 is located at the distal end 62 of the catheter 10, adjacent the balloon inflation port 66. A thermistor (not shown) is positioned inside the lumen 18 carrying thermistor and electrode wires and is mounted in accordance with the manner described in U.S. Pat. No. 4,407,304 entitled "Method of Mounting an Electrical Lead in a Catheter Body" and assigned to the assignee of the present invention. The thermistor is exposed through an opening 70 in the distal end 62 of the catheter 10. The thermistor leads extend through the length of the lumen 18 to the connector 42. The lumen 18 further carries leads attached to electrodes 72, 74, located at the proximal and distal ends 60, 62, respectively, of the catheter tube used in measuring right heart ejection fraction.

Figure 3:
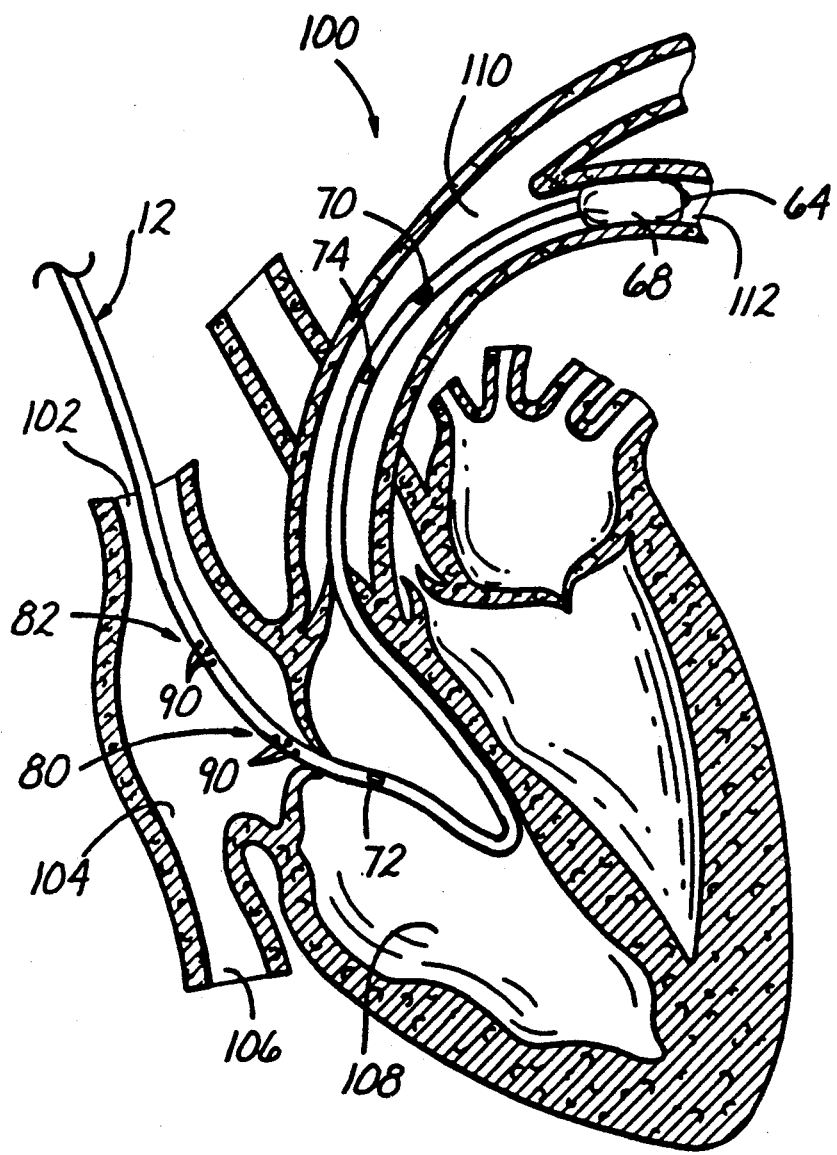
FIG. 3 illustrates the catheter in a wedged position when inserted into a relatively small heart.
Figure 4:
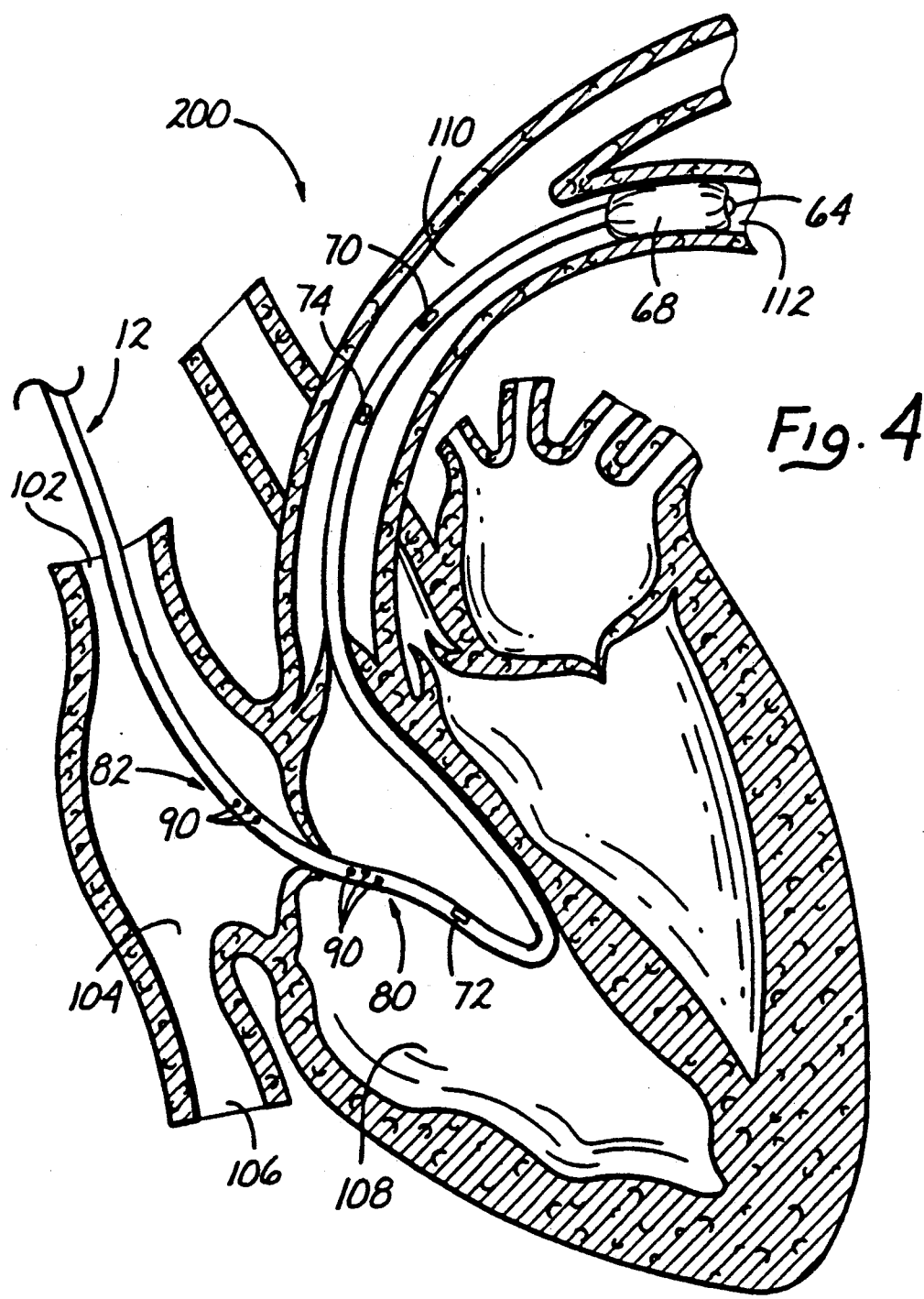
FIG. 4 illustrates the catheter in a wedged position when inserted into a relatively large heart.
Figure 5:
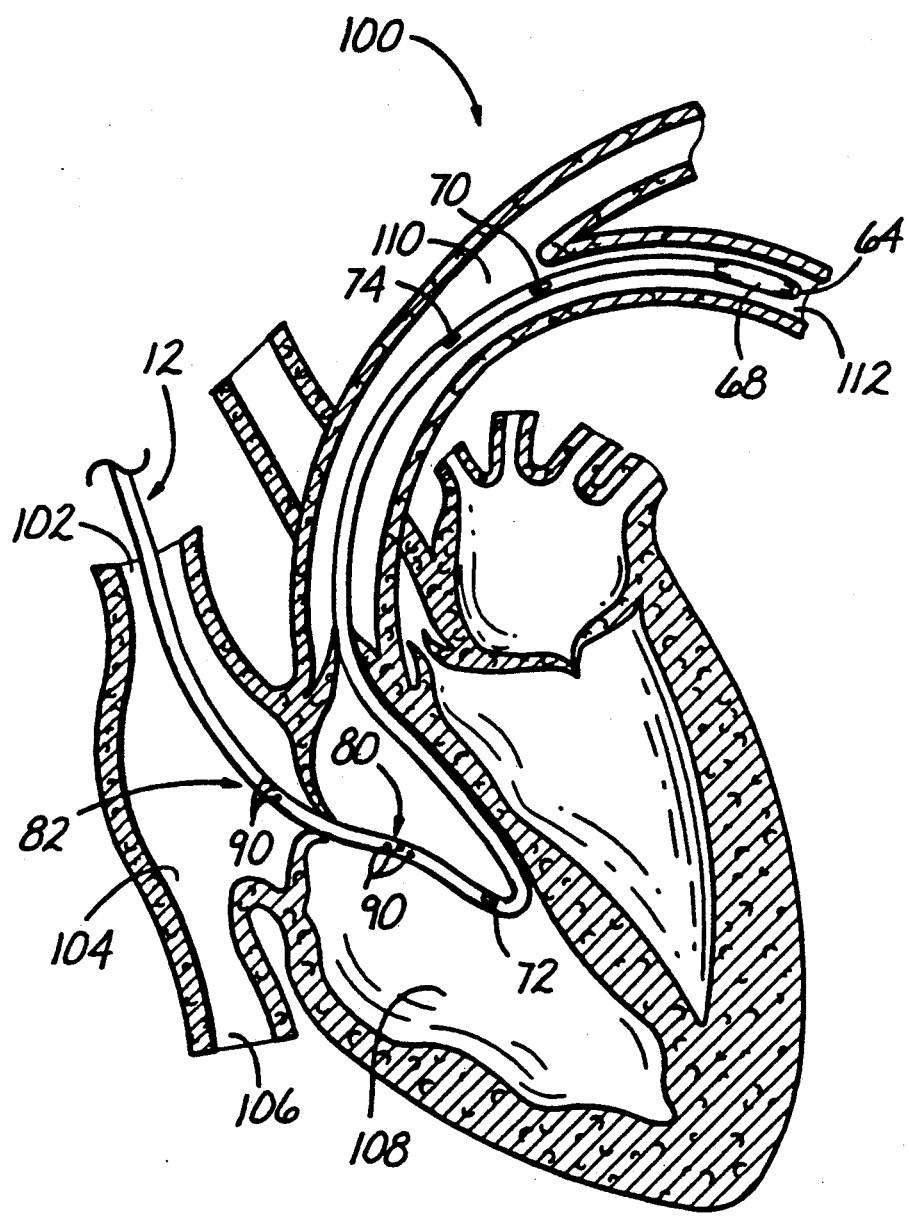
FIG. 5 illustrates the position of the injectate ports in the small heart when forward movement of the catheter occurs.

A first injectate port 80 is formed in a side wall of the catheter 10 in communication with the first injectate lumen 24. A second injectate port 82 is formed in the side wall of the catheter 10, proximate the first injectate port 80, in communication with the second injectate lumen 26. As shown, the first injectate port 80 is located closer to the inflatable balloon 68 than the second injectate port 82. It is desirable that the injectate ports 80, 82 are spaced from each other by about 15-20% of the distance between the first injectate port 80 and the balloon 68. In the preferred embodiment, the injectate ports 80, 82 are spaced apart by approximately 3-4 cm for superior vena cava insertion, such that the first injectate port 80 is located approximately 19 to 21 cm from the balloon 68, and the second injectate port 82 is located approximately 22 to 25 cm from the balloon 68. For inferior vena cava insertion, the spacing between the injectate ports 80, 82 is larger and can be up to 7 cm. The first and second injectate ports 80, 82 preferably comprise a plurality or array of closely spaced openings formed in the side wall of the catheter 10. In the preferred embodiment, each port comprises three round openings 90 (FIGS. 3-5). The openings 90 are offset from each other so that they follow a slightly arcuate path in the side wall of the catheter tube 12, and thereby reduce the possibility of stress induced tears between the openings 90.

As illustrated in FIG. 3 and FIG. 4, the catheter 10 is inserted into a heart 100 through the superior vena cava 102 and into the right atrium 104. Alternatively, the catheter 10 may be inserted into the right atrium 104 through the inferior vena cava 106. Once within the right atrium 104, the balloon 68 is inflated with air or $CO_2$ exiting through the inflation port 66 adjacent the distal tip to inflate the balloon 68, which then carries the catheter 10 with the bloodstream through the right ventricle 108 and into the main pulmonary artery 110. Inside the main pulmonary artery 110, the catheter 10 is advanced until the balloon 68 reaches a wedged position within an individual pulmonary artery 112. In this position, pulmonary artery wedge pressure measurements may be taken at the distal port 64 in accordance with conventional pressure monitoring techniques. After the desired wedge pressure measurements have been obtained, the balloon 68 is then deflated.

When inserted as described above into a patient having a small heart 100, illustrated in FIG. 3, the first injectate port 80 is positioned in the right atrium 104, approximately within 2-5 cm proximate the tricuspid valve 120, while the second injecate port 82 is located farther back in the right atrium 104 as shown. Once the balloon 68 has been deflated, conventional thermodilution techniques may be implemented to obtain measurements and data from which cardiac output and right heart ejection fraction can be determined. To determine cardiac output and/or right heart ejection fraction utilizing thermodilution techniques, cold saline injectate is injected into the heart through the first injectable lumen 24 and discharged through the plural openings 90 comprising the first injectate port 80. The plural openings 90 allow the injectate to become well mixed with the countercurrent blood flow from the inferior vena cava 106 prior to entering the right ventricle 108. The blood flow from the superior vena cava 102 holds the mixture in the right atrium 104 above the tricuspid valve 120, such that when the valve 120 is opened, substantially all the mixture is discharged into the right ventricle 108 and travels through the pulmonary artery 110 past the thermistor. In accordance with well-known techniques, temperature information obtained by the thermistor is transmitted through the leads contained in the first insulation tube 40 and to suitable monitoring devices via the coupler 50.

As illustrated in FIG. 4, if the catheter 10 is inserted in a patient having a larger size heart 200, a greater portion of the length of the catheter 10 will need to be inserted in order to locate the balloon 68 in a wedged position within the pulmonary artery 110. In the larger heart 200, the second injectate port 82 is then positioned within the desired 2-5 cm proximal the tricuspid valve 120. In this position, the first injectate port 80 will typically be located substantially in the right ventricle 108, and thus this port 80 will not be properly located for thermodilution purposes. Accordingly, for large hearts, thermodilution to obtain cardiac output or right heart ejection fraction measurements is implemented using the second injectate port 82. A cold saline injectate is injected through the second injectate lumen 26 and discharged through the openings 90 comprising the second injectate port 82. The injectate mixes with the blood flow and travels through the heart 200 past the thermistor located at the distal end 62 of the catheter tube 12 in the pulmonary artery 110. As previously described, the thermistor transmits temperature information through the coupler 50 to suitable monitoring devices from which cardiac output and/or right heart ejection fraction can be determined. The first injectate port 80 located in the right ventricle 108 gives RV pressure volume relations for systolic and diastolic RV function definition simultaneously to right ventricle ejection fraction measurement.

With the dual injection ports 80, 82 of the present invention, the difficulties associated with manual positioning of a single injectate port relative the tricuspid valve 120 are virtually eliminated. Due to the ease of positioning the catheter of the present invention, valuable physician time is decreased and risks associated with moving the catheter, such as wall perforation are significantly decreased.

Occasionally, forward migration of the catheter 10 can occur after the balloon 68 is deflated. Such migration, due, e.g., to the pulsating action of the heart, can cause an unintended change in position of the injectate ports 80, 82 relative to the tricuspid valve 120. FIG. 5 illustrates catheter position within the small heart 100 when movement of the catheter 10 within the heart 100 after balloon deflation occurs. In this situation, the first injectate port 80 is no longer located in the optimum position relative the tricuspid valve 120, i.e., the first port 80 will be shifted to a location in the right ventricle. Such a condition can be readily detected by monitoring the pressure measurements taken at the injectate ports to determine a shift in port location from the position in the right atrium 104 to a position in the right ventricle 108. With the dual port design of the present invention, this migration in the small heart will then bring the second port 82 into a position proximal the valve 120, and thermodilution can be implemented by injecting fluid through the second injectate lumen 26 to be discharged through the second injectate port 82, thereby saving physician time and reducing the risks associated with major repositioning of the catheter.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to embraced within their scope.

What is claimed is:

1. A method of using a thermodilution catheter having a plurality of injectate ports comprising:
   a. inserting said thermodilution catheter into the heart of a patient;
   b. positioning at least a first of said plural injectate ports in said catheter proximal to the tricuspid valve of the heart;
   c. positioning at least a second of said plural injectate ports upstream from said first injectate port with respect to the direction of blood flow;
   d. discharging fluid through only said first injectate port.

2. The method of claim 1, additionally comprising:
   subsequent to steps (a), (b), (c) and (d), detecting a change in position of said first injectate port relative to said tricuspid valve; and
   discharging fluid through only said second injectate port.

3. The method of claim 2, wherein said change in position is caused by action of the patient's heart on the catheter.

4. The method of claim 2, wherein said change in position is determined by monitoring pressure to detect a shift of said first injectate port from the right atrium of the heart to the right ventricle of the heart.

* * * * *